(12) United States Patent
Song

(10) Patent No.: US 10,408,962 B2
(45) Date of Patent: Sep. 10, 2019

(54) NMR IN KINETICS OF HYDROCARBON GENERATION

(71) Applicant: ConocoPhillips Company, Houston, TX (US)

(72) Inventor: Yishu Song, Houston, TX (US)

(73) Assignee: ConocoPhillips Company, Houston, TX (US)

( * ) Notice: Subject to any disclaimer, the term of this patent is extended or adjusted under 35 U.S.C. 154(b) by 398 days.

(21) Appl. No.: 15/215,403

(22) Filed: Jul. 20, 2016

(65) Prior Publication Data

US 2017/0031051 A1     Feb. 2, 2017

Related U.S. Application Data

(60) Provisional application No. 62/197,859, filed on Jul. 28, 2015.

(51) Int. Cl.

| | |
|---|---|
| *G01V 3/14* | (2006.01) |
| *E21B 41/00* | (2006.01) |
| *E21B 49/02* | (2006.01) |
| *G01N 24/08* | (2006.01) |
| *G01N 33/24* | (2006.01) |
| *G01V 3/38* | (2006.01) |
| *G01R 33/46* | (2006.01) |
| *G01R 33/56* | (2006.01) |

(52) U.S. Cl.
CPC ............ *G01V 3/14* (2013.01); *E21B 41/0092* (2013.01); *E21B 49/02* (2013.01); *G01N 24/081* (2013.01); *G01N 24/085* (2013.01); *G01N 33/241* (2013.01); *G01R 33/46* (2013.01); *G01R 33/4641* (2013.01); *G01V 3/38* (2013.01); *G01R 33/4608* (2013.01); *G01R 33/5605* (2013.01)

(58) Field of Classification Search
CPC ............................. G01V 3/14; E21B 41/0092
USPC .......................................................... 324/309
See application file for complete search history.

(56) References Cited

U.S. PATENT DOCUMENTS

| | | | |
|---|---|---|---|
| 7,011,154 B2 * | 3/2006 | Maher ................... | C09K 8/592 166/245 |
| 7,344,889 B2 * | 3/2008 | Kelemen .............. | G01N 33/241 436/29 |
| 8,967,249 B2 * | 3/2015 | Akkurt .................. | E21B 49/088 166/250.02 |

OTHER PUBLICATIONS

International Search Report for parent case, App. No. PCT/US2016/043182, dated Sep. 22, 2016.
Smernik, R.J., Oades, J.M., Geoderma 96 (2000) 159.
Smernik, R.J., Oades, J.M., "Spin accounting and Restore—two new methods to improve quantitation in solid-state 13C NMR analysis of soil organic matter." Eur. J. Soil Sci. 54 (2003) 103.
Smernik, R.J., Oades, J.M., "The use of spin counting for determining quantitation in solid state 13 C NMR spectra of natural organic matter: 1. Model systems and the effects of paramagnetic impurities." Geoderma 96 (2000) 101.

(Continued)

*Primary Examiner* — Reena Aurora
(74) *Attorney, Agent, or Firm* — Boulware & Valoir

(57) ABSTRACT

Disclosed are methods of characterizing kerogen and its hydrocarbon generation potential using NMR as the primary analytical tool, and using such data to derive the kinetics of hydrocarbon generation and alteration, thus predicting the hydrocarbon potential of source rock in geological setting, which can then be used in petroleum exploration and production.

19 Claims, 5 Drawing Sheets

(56) References Cited

OTHER PUBLICATIONS

Petsch, et el., A solid state 13C-NMR study of kerogen degradation during black shale weathering, Geochimica et Cosmochimica Acta, vol. 65, No. 12, pp. 1867-1882 (2001).

Smernik R.J., et al., Assessing the quantitative reliability of solid-state 13C NMR spectra of kerogens across a gradient of thermal maturity, Solid State Nuclear Magnetic Resonance 29 (2006) 312-321.

Hillier, Pyrolysis Kinetics and Chemical Structure Considerations of a Green River Oil Shale and Its Derivatives, dissertation submitted to the faculty of Brigham Young University in partial fulfillment of the requirements for the degree of Doctor of Philosophy, Mar. 16, 2011, pp. 33, 34, 41, 47, 52, 61-62, 99, 117, 126-128.

\* cited by examiner

|  | A | B | C |
|---|---|---|---|
| Atomic H-C | 1.65 | 1.28 | 0.84 |
| Atomic O-C | 0.06 | 0.10 | 0.13 |
| Hydrocarbons | Oil | Oil + Gas | Gas |

NMR IN KINETICS OF HYDROCARBON GENERATION

PRIOR RELATED APPLICATIONS

This application claims priority to U.S. Ser. No. 62/197,859, filed Jul. 28, 2015 and incorporated by reference herein in its entirety for all purposes.

FEDERALLY SPONSORED RESEARCH STATEMENT

Not applicable.

FIELD OF THE DISCLOSURE

The invention relates to methods, apparatus and systems to derive the kinetics of hydrocarbon generation from kerogens and subsequent alterations in the hydrocarbons, using nuclear magnetic resonance (NMR) analysis as the primary tool to assist in devising a network of chemical reactions and obtaining associated kinetics parameters. Prediction of petroleum fluid quality and quantity is of paramount importance in petroleum exploration. Such predictions are mostly attempted via basin modeling, in which kinetics of hydrocarbon generation and alteration are the most critical input.

BACKGROUND OF THE DISCLOSURE

To assess the timing of petroleum generation and predict the quantity and quality of petroleum fluids subsurface are pivotal in petroleum exploration. Petroleum fluid is generated from kerogen, which by definition is the fraction of organic matter in sedimentary rocks that is insoluble in usual organic solvents. Kerogen is a complex mixture of macromolecular materials, whose composition and structure evolve over geological time under the influence of burial temperature and pressure.

With the demise of living matter, such as diatoms, planktons, spores and pollens, organic matter begins to undergo decomposition or degradation. In this break-down process, large biopolymers from proteins and carbohydrates begin to dismantle either partially or completely. These dismantled components are units that can then polycondense to form polymers. This polymerization usually happens alongside the formation of a mineral component (geopolymer) resulting in a sedimentary rock, such as kerogen shale. The formation of polymers in this way accounts for the large molecular weights and diverse chemical compositions associated with kerogen. The smallest units are the fulvic acids, the medium units are the humic, and the largest units are the humins. See FIG. 1A-D.

When organic matter is contemporaneously deposited with geologic material, subsequent sedimentation and progressive burial or overburden provides significant pressure and a temperature gradient. When these humic precursors are subjected to sufficient geothermal pressures for sufficient geologic time, they begin to undergo certain specific changes to become kerogen. Such changes are indicative of the maturity stage of a particular kerogen. These changes include loss of hydrogen, oxygen, nitrogen, and sulfur, which lead to loss of other functional groups that further promote isomerization and aromatization which are associated with increasing depth or burial. Aromatization then allows for neat molecular stacking in sheets, which in turn increases molecular density and vitrinite reflectance properties, as well as changes in spore coloration, characteristically from yellow to orange to brown to black with increasing depth.

As kerogen is a mixture of organic material, rather than a specific chemical, it cannot be given a chemical formula. Indeed its chemical composition can vary quite distinctively from sample to sample. Thus, kerogen is typed according to average content.

Type I: Sapropelic.

Type 1 kerogen oil shales yield larger amount of volatile or extractable compounds than other types upon pyrolysis. Hence, from the theoretical view, Type 1 kerogen oil shales provide the highest yield of oil and are the most promising deposits in terms of conventional oil retorting, containing alginite, amorphous organic matter, cyanobacteria, freshwater algae, and land plant resins. Typical features include:

Hydrogen:carbon ratio>1.25
Oxygen:carbon ratio<0.15
Shows great tendency to readily produce liquid hydrocarbons
Derives principally from lacustrine algae and forms only in anoxic lakes and several other unusual marine environments
Has few cyclic or aromatic structures
Formed mainly from proteins and lipids Type II: Planktonic:

Type II kerogen is common in many oil shale deposits. It is based on marine organic materials, which are formed in reducing environments. Sulfur is found in substantial amounts in the associated bitumen and is generally higher than the sulfur content of Type I or III kerogens. Although pyrolysis of Type II kerogen yields less oil than Type I, the amount acquired is still sufficient to consider Type II bearing rocks as potential oil sources. Typical features of Type II kerogen include:

Plankton (marine)
Hydrogen:carbon ratio<1.25
Oxygen:carbon ratio 0.03 to 0.18
Tend to produce a mix of gas and oil.
Great tendencies to produce petroleum and are all formed from lipids deposited under reducing conditions.
Several types:
  Sporinite: formed from the casings of pollen and spores
  Cutinite: formed from terrestrial plant cuticle
  Resinite: formed from terrestrial plant resins and animal decomposition resins
  Liptinite: formed from terrestrial plant lipids (hydrophobic molecules that are soluble in organic solvents) and marine algae Type II: Sulfurous:
Similar to Type II but high in sulfur.

Type III: Humic:

Kerogen Type III is formed from terrestrial plant matter that is lacking in lipids or waxy matter. It forms from cellulose, the carbohydrate polymer that forms the rigid structure of terrestrial plants, lignin, a non-carbohydrate polymer formed from phenyl-propane units that binds the strings of cellulose together, and terpenes and phenolic compounds in the plant. Type III kerogen involving rocks are found to be the least productive upon pyrolysis and probably the least favorable deposits for oil generation. Type III kerogen features include:

Land plants (coastal)
Hydrogen:carbon ratio<1
Oxygen:carbon ratio 0.03 to 0.3
Material is thick, resembling wood or coal Tends to produce coal and gas, although recent research has shown that type III kerogens can actually produce oil under extreme conditions Has very low hydrogen content because of the extensive ring and aromatic systems Type IV: Residue:

Type IV kerogen contains mostly decomposed organic matter in the form of polycyclic aromatic hydrocarbons. They have no potential to produce hydrocarbons. Features include a hydrogen to carbon ratio of <0.5.

As part of the evolution of kerogen, petroleum fluid is generated, a process referred as primary cracking. Also under the influence of burial temperature and pressure, the generated petroleum fluid itself evolves to increasingly lighter fluid via a series of reactions, a process referred as secondary cracking.

As any chemical reaction, the primary cracking and secondary cracking proceed at finite rates governed by reaction kinetics. The practice to derive the parameters that describe the kinetics of petroleum generation is generally referred as "source rock kinetics analysis" or "kerogen kinetics analysis." Once derived correctly, kinetics is applied in geological settings to predict petroleum generation, as well as its alteration, quantity and quality.

Over the past decades, significant efforts have been dedicated to developing methods that are suitable to derive the kinetics of petroleum generation and alteration of generated petroleum, e.g. changing from black oil to volatile oil, in either petroleum source rock or the reservoir. Catering for different business needs, a few methods are available. The most widely used method is the bulk kinetics analysis based on programmed open system pyrolysis.

In bulk kinetics analysis, source rock or kerogen isolate sample is pyrolyzed at certain heating rate under an inert gas (e.g. helium or nitrogen) purge, which transfers the pyrolysis products to a FID for continuous measuring of hydrocarbons generated as pyrolysis proceeds. After performing this experiment by using a few different heating rates (typically from 0.1° C./min to 20° C./min), the bulk hydrocarbon generation kinetic parameters can be derived based on the measured hydrocarbon generation curves at different heating rates. This method is relatively cheap and fast, but only provides kinetic parameters for the overall transformation of kerogen to petroleum fluid, not compositional kinetics. Due to its open system nature, the pyrolysis products do not closely represent hydrocarbons generated subsurface.

To derive compositional kinetics based on bulk kinetics analysis, another technique, named MicroScale Sealed Vessel (MSSV) pyrolysis has been developed. In MSSV a number of small quartz vials, each of which is sealed with known amount of kerogen sample, are pyrolyzed at selected heating rates to selected end temperatures. Upon thermolysis, each vial is cracked open in a GC sampler and the products are analyzed directly by GC. Based on the product compositions of a series of MSSV experiments, a compositional kinetics model is derived from bulk kinetics by subdividing activation energy (Ea) with respect to its contribution to the generation of individual components. Strictly speaking MSSV approach is only semi-compositional, since it can only analyze products detectable by GC, leaving out heavier products. Also, it has limited ability to tackle secondary cracking.

Gold tube thermolysis is a more sophisticated compositional kinetics analysis method, in which kerogen or whole rock sample is sealed into a gold tube under inert atmosphere, and the sealed gold tubes are thermolyzed while being subjected to a confining pressure (to mimic subsurface conditions). After thermolysis of a series of tubes over a range of thermal stresses, detailed analyses are performed for gas, liquid and solid products generated in each tube. Based on the product composition changes over a range of thermal stresses (different combinations of temperature and time), a compositional kinetics model is derived via numerical regression/optimization of the experimental data. This numerical analysis process involves designing a reaction network, which describes the chemical changes and deriving the kinetics parameters for the reaction network.

During Rock-Eval analysis, whole rock or kerogen isolate sample is pyrolyzed using a programmed heating while being purged by an inert gas, e.g. helium or nitrogen, which carries the pyrolysis products to the detector. The pyrolysis products are carried by the purge gas to detectors. A flame ionization detector (FID) detects hydrocarbons released during each stage of heating. Infrared (IR) detector measures CO and $CO_2$ released during pyrolysis and oxidation. A thermocouple monitors temperatures, and these measurements are recorded on a chart known as a pyrogram (see FIG. 2).

An exemplary pyrolysis oven temperature program is as follows: for 3 min, the oven is kept isothermally at 300° C. and the free hydrocarbons are volatilized and measured as the $S_1$ peak (detected by FID). The temperature is then increased from 300° to 550° C. (at 25° C./min). This is the phase of volatilization of the very heavy hydrocarbons compounds (>$C_{40}$) as well as the cracking of nonvolatile organic matter. The hydrocarbons released from this thermal cracking are measured as the $S_2$ peak (by FID). The temperature at which $S_2$ reaches its maximum depends on the nature and maturity of the kerogen and is called $T_{max}$. The $CO_2$ released from kerogen during pyrolysis in the 300°-390° C. temperature range is cold trapped first, then released warming up the cold trap and detected on a TCD ($S_3$ peak).

In summary, the four key parameters obtained by Rock Eval are as follows:

$S_1$=the amount of free hydrocarbons (gas and oil) in the sample (in milligrams of hydrocarbon per gram of rock).

$S_2$=the amount of hydrocarbons generated through thermal cracking of kerogen and nonvolatile organic matter. $S_2$ is the indication of generative potential and used to calculate hydrogen index (HI).

$S_3$=the amount of $CO_2$ (in milligrams $CO_2$ per gram of rock) produced during pyrolysis of kerogen. $S_3$ is an indication of the amount of oxygen in the kerogen and is used to calculate the oxygen index. Contamination of the samples should be suspected if abnormally high $S_3$ values are obtained. High concentrations of carbonates that break down at lower temperatures than 390° C. will also cause higher $S_3$ values than expected.

$T_{max}$=the temperature at which the $S_2$ signal peaks. $T_{max}$ is an indication of the maturity.

The RE II apparatus can also be used to determine the total organic carbon or "TOC" of the sample by oxidizing (in an oxidation oven kept at 600° C.) the organic matter remaining in the sample after pyrolysis (residual organic carbon). The TOC is then determined by adding the residual organic carbon detected to the pyrolyzed organic carbon, which in turn is measured from the hydrocarbon compounds issuing from pyrolysis.

Currently used bulk kinetics and MSSV based compositional kinetics are inadequate for advanced fluids quality and property predictions. Gold tube thermolysis generates products better matching subsurface fluids, but compositional kinetics analysis based on gold tube thermolysis is too time-consuming and also prone to error. Thus, what is needed in the art is a better method of quickly and efficiently determining the compositional kinetics of hydrocarbon generation from kerogen and subsequent alterations of generated petroleum fluids.

SUMMARY OF THE DISCLOSURE

This disclosure provides a novel methodology to derive compositional kinetics of hydrocarbon generation from kerogen and subsequent changes of generated petroleum fluids, by using nuclear magnetic resonance (NMR) as the primary analytical technique, complementing other existing techniques.

Current kinetics analysis methods are either laborious or inadequate, particularly regarding the mass balance of hydrogen. In this invention, the maturation of kerogen and petroleum generation is described as a process of redistribution of hydrogen among hydrogen-enriched species and hydrogen-depleted species. This process is experimentally monitored by NMR and numerically modeled with tight constrains of carbon and hydrogen mass balances. Source rock and/or isolated kerogen of different maturities (natural or artificial maturation) will be analyzed by NMR for the compositional changes, including relative abundances of hydrogen in saturates vs. aromatics, aliphatic carbon vs. aromatic carbon, carbon with and without bonded hydrogen. These changes will then be numerically modeled following chemical kinetic laws. Thus, derived kinetics parameters will be used to predict hydrocarbon generation (quantity, quality and timing) subsurface. This information can then be used in developing and executing a plan to access the hydrocarbons.

The inclusion of NMR techniques in the analysis of kerogen will allow us to more accurately derive kinetics parameters of hydrocarbon generation. Kerogen maturation and hydrocarbon generation can be described as a redistribution process of hydrogen among hydrogen enriched species (oil and gas) and hydrogen-depleted species (coke). The rate of hydrogen redistribution and the resulted concentration changes of different species are governed by kinetics of the chemical reactions and, to certain extent by thermodynamics at high maturity stage. We can model this process using a network of first order parallel reactions, as currently used, or as a network of parallel plus sequential reactions of different orders, which has not been previously implemented. Traditional kinetics analysis methods have poor constraints on the mass balance of hydrogen. By directly monitoring the changes of abundances of H and C at different chemical environments (structures), NMR analysis allows tighter control on C and H mass balances, thus improving the numerical implementation of reaction networks.

NMR spectroscopy complements other kerogen analytical methods in several ways. A description of the whole kerogen sample is obtained, compared with only the pyrolysis- and GC-amenable fraction revealed by pyrolysis-gas chromatography (Py-GC). NMR provides greater specificity in carbon bond types and improved quantification over IR spectroscopy.

In more detail, the invention includes any one or more embodiments in any combination(s) thereof:

A method of determining hydrocarbon generation potential from kerogen, said method comprising:

a) obtaining a sample kerogen;
b) performing elemental analysis on a portion of said kerogen to determine its C, H, N, S and O content;
c) performing NMR analysis on a portion of said kerogen to determine its initial relative abundances of different H and C species;
d) pyrolyzing a portion of said isolated kerogen to determine a pyrolysis temperature profile and to produce petroleum fluid and a kerogen residue;
e) analyzing the composition of said petroleum fluid;
f) performing NMR analysis on said kerogen residue; and
g) predicting hydrocarbon generation from said kerogen using the data obtained in steps b-f to determine the hydrocarbon generating potential of said kerogen; and
h) using said hydrocarbon generating potential in formulating and executing plans to explore and produce hydrocarbons.

A method of analyzing kerogen, said method comprising:

a) obtaining a sample of kerogen;
b) performing elemental analysis on a portion of said kerogen to determine its C, H, N, S and O content;
c) performing NMR analysis on a portion of said kerogen to determine its initial relative abundancesof different H and C species;
d) pyrolyzing a portion of said kerogen to determine a pyrolysis temperature profile and to produce a mixture of petroleum fluid and a kerogen residue;
e) analyzing the composition of said petroleum fluid; and
f) performing NMR analysis on said kerogen residue.

A method of predicting hydrocarbon generation potential from kerogen, said method comprising:

a) obtaining a sample of kerogen;
b) performing elemental analysis on a portion of said sample of kerogen to determine a H, C, N, O and S content of said kerogen;
c) performing NMR analysis on a portion of said sample of kerogen to determine aliphatic and aromatic percentages of said kerogen;
d) pyrolyzing a portion of said sample of kerogen to determine a pyrolysis temperature profile of said sample of kerogen and to produce petroleum fluid and a kerogen residue;
e) analyzing the composition of said petroleum fluid;
f) performing NMR analysis on said kerogen residue; and
g) predicting hydrocarbon generation potential from said kerogen using the data obtained in steps b-f.

| A method of determining hydrocarbon generation potential from kerogen, said method comprising: |
|---|
| a) obtaining a sample of source rock containing kerogen;
b) grinding said source rock to produce a powder;
c) extracting said powder to produce isolated kerogen;
d) performing elemental analysis on a portion of said isolated kerogen to determine its C, H, N, S and O content;
e) performing NMR analysis on a portion of said isolated kerogen to determine its initial relative abundances of different H and C species;
f) pyrolyzing a portion of said isolated kerogen to determine a pyrolysis temperature profile and to produce a mixture of petroleum fluid and a kerogen residue;
g) analyzing the composition of said petroleum fluid;
h) performing NMR analysis on said kerogen residue; and
i  predicting hydrocarbon generation potential from said kerogen using the data obtained in steps d-h and using a network of I reactions; and
j) using said hydrocarbon generating potential in formulating and executing plans to explore and produce hydrocarbons.
The method of any claim herein, wherein said NMR analysis is solid state NMR.
The method of any claim herein, wherein said NMR analysis uses $^{13}$C NMR.
The method of any claim herein, wherein said NMR analysis uses $^{1}$H NMR.
The method of any claim herein, wherein said NMR analysis uses $^{15}$N NMR.
The method of any claim herein, wherein said NMR analysis uses both $^{13}$C and $^{1}$H NMR.
The method of any claim herein, wherein said NMR analysis is solid-state magic angle spinning (MAS) NMR.
The method of any claim herein, wherein said NMR analysis is solid state NMR using cross polarization (CP).
The method of any claim herein, wherein said NMR analysis is solid state NMR using direct polarization (DP).
The method of any claim herein, wherein said NMR analysis is solid state NMR using both CP and DP.
The method of any claim herein, wherein said method uses spin counting to calibrate NMR data.
The method of any claim herein, wherein predicting step uses a network of first order parallel reactions. The method of any claim herein, wherein predicting step uses higher order parallel reactions plus sequential reactions. Combinations are also contemplated.
The method of any claim herein, wherein predicting step uses the Arrhenius equation.
The method of any claim herein, wherein said pyrogram can be read to determine S1, S2, S3, and Tmax.
The method of any claim herein, wherein said identifying step also uses NMR.
The method of any claim herein, wherein said identifying step uses gas chromatography or mass spectrometry or a combination thereof.
The method of any claim herein, wherein gold vessel thermolysis of a portion of said isolated kerogen is performed in parallel with NMR step as a double check of the data quality. |

NMR analysis may be conducted using a solid state NMR, $^{13}$C NMR, $^{1}$H NMR, $^{15}$N NMR, both $^{13}$C and $^{1}$H NMR, or any combination thereof. Additionally, solid-state magic angle spinning (MAS) NMR, cross polarization (CP) NMR, direct polarization (DP) NMR, both CP and DP, or combinations thereof can be used. Spin counting may be used to calibrate NMR data.

Modeling may include a network of first order parallel reactions, higher order parallel reactions plus sequential reactions, Arrhenius equation, or combinations thereof.

Gas chromatography and/or mass spectrometry may be used to analyze the petroleum fluids produced from maturing the kerogen, the kerogen residue, and other samples. NMR can be used as well.

As used herein, the term "kerogen" refers to complex fossilized organic material, found in oil shale and other sedimentary rock that is insoluble in common organic solvents and yields petroleum products on distillation.

As used herein, different maturity stages of source rock and/or kerogen isolate samples can be either artificial or natural. "Artificial" means we perform thermolysis experiment as described above in the lab to artificially mature the kerogen. "Natural" means we used geological samples of different maturities.

As used herein, "petroleum fluids" means hydrocarbon liquids and/or gases produced by maturing or artificially maturing kerogen.

As used herein "E&P" means exploration and production. An "E&P plan" is used in decided where and how to drill for E&P.

In "executing" an E&P plan, what is meant are those typical surface and subsurface activities that allow hydrocarbon and/or kerogen to be brought to the surface for either evaluation or production, and plans that include some degree of in situ conversion are also included herein. It is recognized that the data generated herein is used to formulate E&P plans, and may or may not be directly used in drilling and production of hydrocarbon, but the data is indirectly used to the extent that E&P plans are used in drilling and production, and that is intended to be included herein.

By "hydrocarbon generating potential", we mean to include all of the parameters pertinent to hydrocarbon generation and subsequent alteration with respect to both quantity (volume of hydrocarbon) and quality, e.g. gas oil ratio (GOR), density (API gravity), and the like.

It is recognized that a single party typically will not perform all of the steps of a method, and that sample collection, lab experiments, numerical analysis/modeling and subsequent E&P plan execution may be performed by different contractors or service providers. However, all of such activities are typically at the request of the resource developer, and these actions can thus be imputed to the developer. Therefore, directly performing a step, or indirectly performing a step through a contractor or service provider, is intended to be included within the scope of the claims.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| ATM | Atmosphere |
| FID | Flame ionization detector |
| GC | Gas chromatography |
| HI | hydrogen index = 100 × S2/TOC |
| IR | Infrared |
| MS | Mass spectrometry |
| NMR | Nuclear Magnetic Resonance |
| OI | oxygen index = 100 × S3/TOC |
| P | Pressure |
| PI | production index, = S1/(S1 + S2) |
| PP | Petroleum potential = S1 + S2. |
| PVT | Pressure, volume, temperature |
| RE | Rock Eval |
| T | Temperature |
| TCD | Thermal conductivity detection |
| Tmax | Pyrolysis over temperature during maximum generation of hydrocarbons. |
| TOC | Total Organic Carbon |
| VCT | variable contact time |
| VR | vitrinite reflectance |
| VSL | variable spin lock |

BRIEF DESCRIPTION OF THE DRAWINGS

FIG. 1A-D Exemplary compounds in kerogen wherein FIG. 1A is Algal kerogen, FIG. 1B is Liptinitic Kerogen, and FIG. 1C is Humic Kerogen. FIG. 1D displays chemical features of the compounds in A-C.

DETAILED DESCRIPTION

Figure 1A:
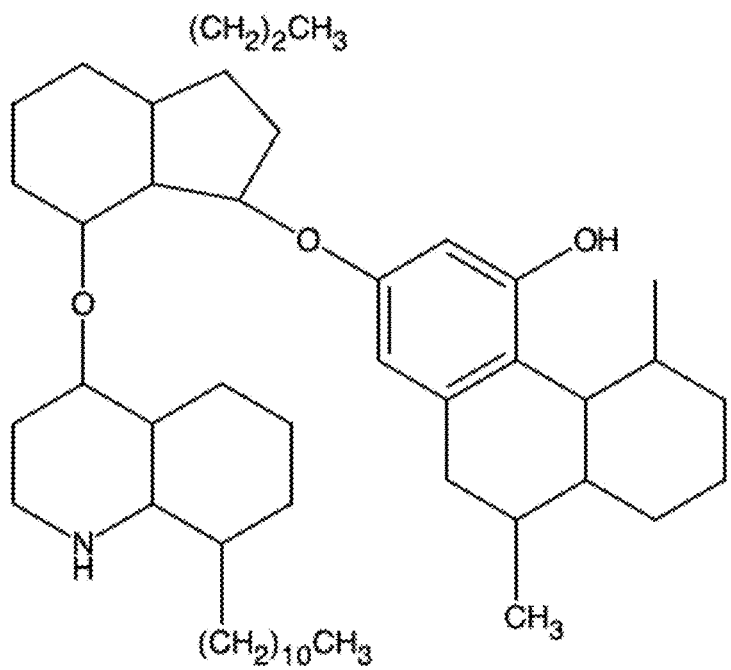
Figure 1B:
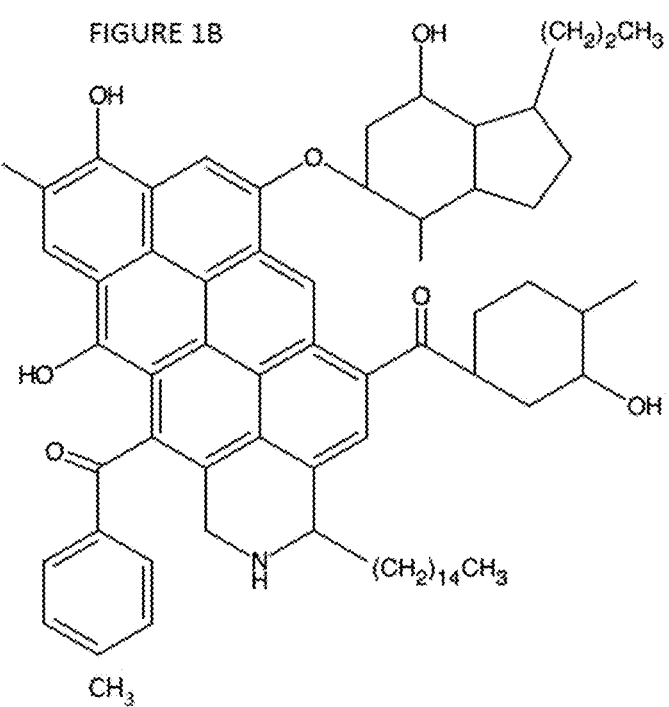
Figures 1C, 1D:
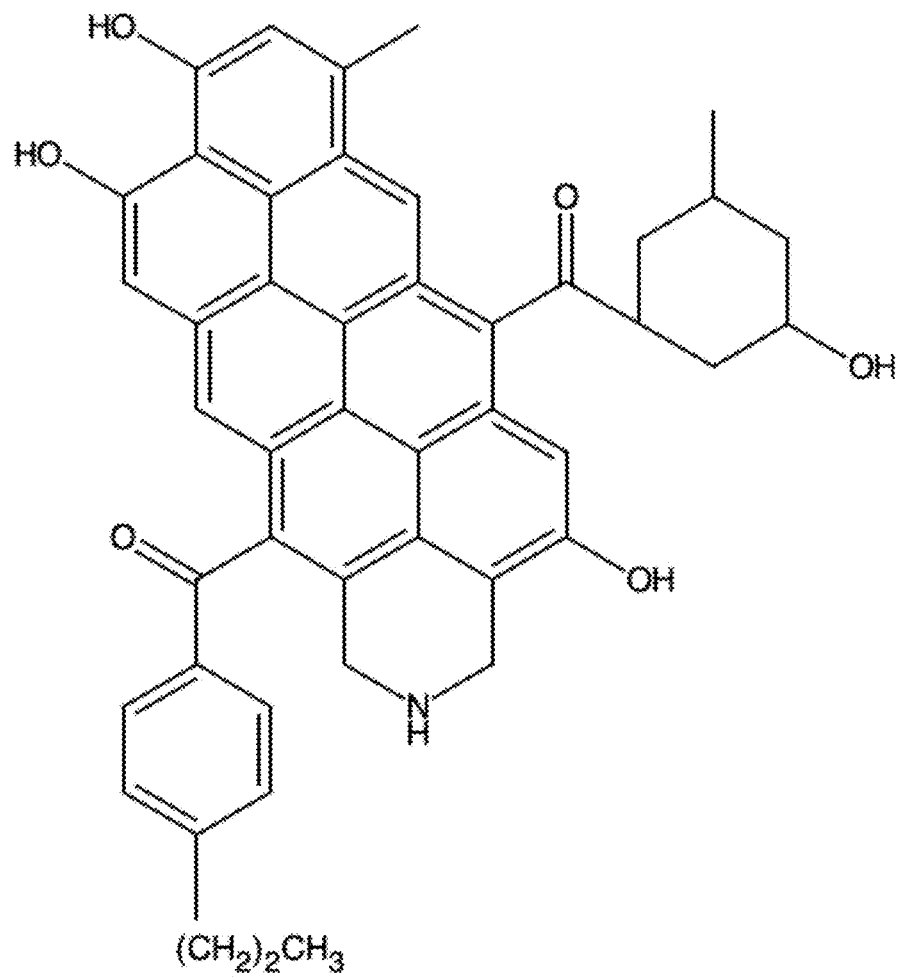
Figure 2:
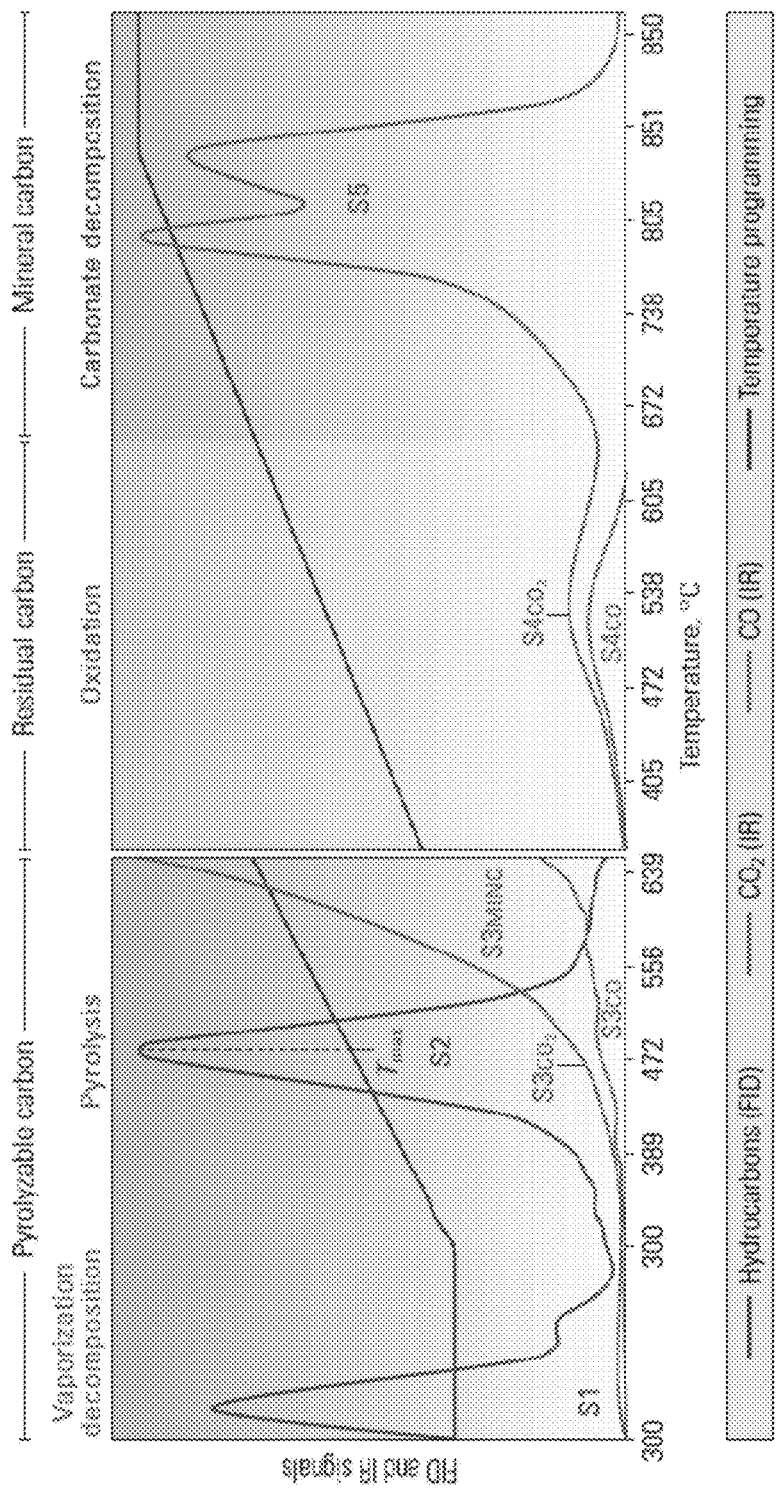
FIG. 2 is a pyrogram to determine the amount of pyrolyzable carbon, residual carbon and TOC. Free hydrocarbons are measured by the S1 peak and residual hydrocarbons are measured by the S2 peak. $T_{max}$ of 472° C. corresponds to the temperature recorded when the S2 peak was achieved. CO, $CO_2$, and mineral carbon components of the S3 measurements are also displayed. $CO_2$ is proportional to the amount of a oxygen present in organic matter and provides input for calculating an important index used in determining maturity and kerogen type.
Figure 3:
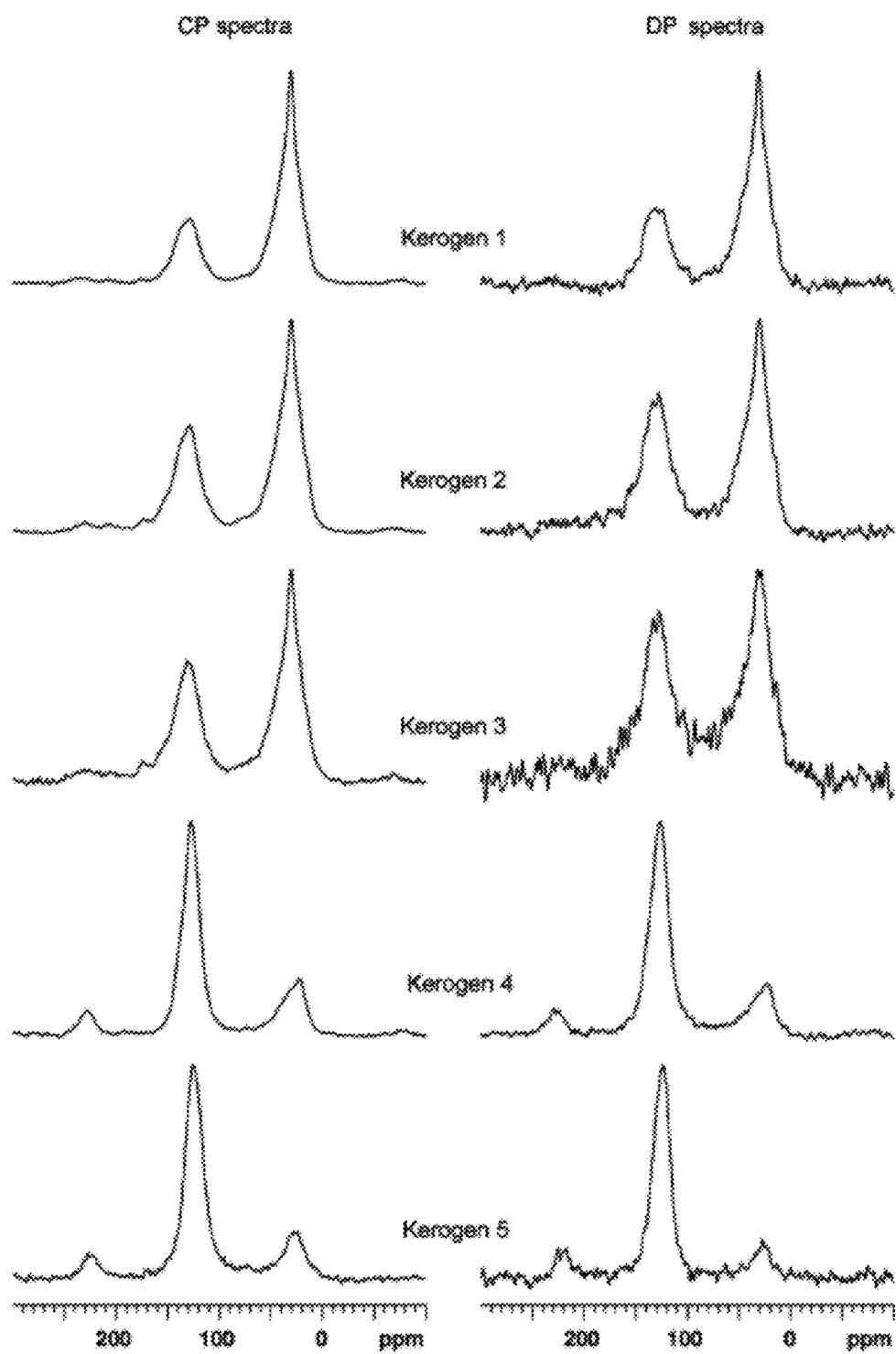
FIG. 3 Exemplary kerogen spectra. From Smermik 2006.

The disclosure provides a novel method, apparatus and system for accurately predicting hydrocarbon generation from kerogen and subsequent alteration. Hydrocarbon generation kinetics are typically derived by open system or closed system pyrolysis followed by product analyses, mostly by Rock-Eval, GC and GC/MS. However, these methods do not provide very accurate C and H mass balances. Thus, we propose to use NMR analysis in this work, thus providing faster turnaround time, as well as improved data for C and H mass balance in kinetics modeling.

The methodology employed can be generally described as follows:
1. Sample Preparation:
   1.a. Select immature source rock containing a sample of interest, or an analog if target source rock is unavailable.
   1.b. Isolate kerogen from immature source rock by first soxhleting the powdered rock with 90:10 dichloromethane/methanol mixture, then removing minerals with acid digestion.
2. Initial Characterization:
2A. Elemental Analysis:
   Perform elemental analysis on the isolated kerogen to determine its C, H, N, S and O content. The initial relative abundance of H and C is thus obtained.
   Elemental analysis or "EA" can be by any method known in the art. The most common form of elemental analysis, CHN analysis, is accomplished by combustion analysis. In this technique, a sample is burned in an excess of oxygen and various traps, collecting the combustion products: carbon dioxide, water, and nitric oxide. The masses of these combustion products can be used to calculate the composition of the unknown sample.
   Other quantitative methods include: 1) Gravimetry, where the sample is dissolved and then the element of interest is precipitated and its mass measured or the element of interest is volatilized and the mass loss is measured. 2) Optical atomic spectroscopy, such as flame atomic absorption, graphite furnace atomic absorption, and inductively coupled plasma atomic emission spectroscopy, which probe the outer electronic structure of atoms. 3) Neutron activation analysis, which involves the activation of a sample matrix through the process of neutron capture. The resulting radioactive target nuclei of the sample begin to decay, emitting gamma rays of specific energies that identify the radioisotopes present in the sample. The concentration of each analyte can be determined by comparison to an irradiated standard with known concentrations of each analyte.
   To qualitatively determine which elements exist in a sample, the methods include Mass spectrometric atomic spectroscopy, such as inductively coupled plasma mass spectrometry, which probes the mass of atoms. Other spectroscopy, which probes the inner electronic structure of atoms such as X-ray fluorescence, particle-induced X-ray emission, X-ray photoelectron spectroscopy, and Auger electron spectroscopy, can also be used
   Chemical methods of elemental analysis are also possible.
2B: Initial NMR Characterization:
   Perform NMR analysis of the immature kerogen and determine its initial relative abundances of different H and C species, e.g. aliphatic vs. aromatic H, C with different numbers of bonded H, and correlate the thus determined H and C abundance to elemental analysis results obtained in step 2A.
3. Thermolysis:
   Artificially mature (thermolysis) the immature kerogen/source rock at certain temperatures in a closed vessel (e.g. quartz tube). The sample vessels preferably have adjustable headspace volume. During thermolysis, sample is compacted and encapsulated into a small volume. After thermolysis, the products can be released into the headspace. Each of the gas, liquid and solid products may be measured and identified by sampling from the closed reaction vessel.

We can adjust headspace volumes to investigate the partitioning of petroleum fluids between free space and kerogen matrix (desorbed free species vs. absorbed species in kerogen under different PVT conditions).

If necessary, other materials, e.g. water, minerals, hydrogen, can be co-encapsulated with kerogen/source rock for thermolysis. Thermolysis of kerogen isolate vs. whole rock, with and without water enable studying different aspects/effects of hydrocarbon generation subsurface over geological time.

4 NMR Analysis:

After thermolysis, the remaining kerogen residue may be analyzed directly by NMR. This will provide information about the hydrogen content of the unconverted kerogen and char-like residue, thus providing how much hydrogen has converted to hydrocarbon fluids.

NMR analyses are performed to determine the abundance changes of H and C in their different chemical environments (e.g. aliphatic vs. aromatic). The overall transformation ratio can be readily and reliably determined by the abundance of C without bonded H (graphite, dead coke), thus a bulk kinetics model can be readily derived. The compound specific H and C NMR signals enable monitoring of composition changes of generated hydrocarbon species (petroleum fluids), which then enables deriving compositional kinetics models.

Unlike current kinetics analysis methods with relatively loose controls on carbon and hydrogen mass balances, kinetics derived from NMR analysis described by this invention have improved mass balance controls on both C and H.

Any method of NMR analysis is possible, including e.g., NMR spectroscopy, Continuous wave (CW) spectroscopy, Fourier transform spectroscopy, Multi-dimensional NMR Spectroscopy and Solid-state NMR spectroscopy. It is known in the art how to obtain high-resolution $^{13}$C and $^{1}$H or even $^{15}$N NMR spectra by solid state NMR, and such may therefore be preferred.

To date, most solid-state $^{13}$C NMR studies of kerogen have involved quantifying signal in a range of chemical shift regions and assigning these to specific functional groups. There is an inherent danger in this approach, due to the fact that the NMR signal of some functional groups can be compromised, especially when the cross polarization (CP) technique is used. This issue has been discussed widely in the coal literature, and has led to the greater use of the more quantitatively reliable direct polarization (DP) technique, otherwise known as Bloch decay or single pulse excitation, and which may thus be preferred. Some workers also recommend a simple calibration procedure called "spin counting" to be very useful for diagnosing NMR quantitation problems in the analysis of organic matter.

5. Calibration:

For calibration purposes, gold vessel thermolysis can be performed in parallel with NMR samples (undergoing the same thermal stresses). Gold tube thermolysis can be conducted with high confining pressure (mimic of overburden subsurface). This is not doable for quartz tube thermolysis. Thus, the gold tube thermolysis can provide a double check of the accuracy of the pyrolysis data. Eventually, we can use quartz tube thermolysis alone to derive compositional kinetics, only correcting the data by gold tube samples if necessary (e.g. under ultra high pressure conditions).

The petroleum fluids generated inside the gold vessel will be extracted out (e.g. by a supercritical fluid extraction system using carbon disulfide or something similar as solvent). The residue will then be analyzed by NMR for the abundances of different H and C. The abundance change of C without bonded H serves as a double check for the bulk kinetics derived from analysis described in step 4.

The extract from the gold tubes can either be analyzed by NMR for its composition, and/or conventional GC and GC-MS for detailed speciation. If there are any differences resulting from different thermolysis vessels (e.g. between quartz tube and gold tube), such differences will allow correlation of chemical changes occurred under different thermolysis environments (quartz vs. gold tube, both are closed systems, but under different pressures during thermolysis).

6. Numerical Analysis:

Kerogen maturation and hydrocarbon generation can be described as a redistribution process of hydrogen among hydrogen enriched species (oil and gas) and hydrogen depleted species (coke). The rate of hydrogen redistribution and the resulted concentration changes of different species are governed by kinetics of chemical reaction and, to certain extent by thermodynamics at high maturity stage.

We can model this process using a network of first order parallel reactions, as currently used, or higher order parallel plus sequential reactions, or combinations thereof. Higher order chemical sequential reactions are more challenging to model by traditional kinetics analysis experiments, particularly stoichiometry and mass balance of hydrogen. NMR analysis, however, with direct monitoring of relative abundances of H and C at different chemical environments (structures), allows much tighter control on C and H mass balances, and better numerical solutions for differential equations describing the evolution of different species. A network of reactions will be devised to describe the evolution of different species.

For each individual member reaction, its reaction rate constant (k) is described by Arrhenius equation:

$$k=Ae^{-Ea/RT}$$

Where A is frequency factor, Ea is activation energy, R is gas constant, and T is temperature in Kelvins.

The whole set of kinetics parameters, including stoichiometry and Arrhenius parameters of each reaction will be determined by non-linear regression with experimental data (e.g. integral of different H and C NMR signals).

Herein we describe an exemplary NMR protocol: Solid-state $^{13}$C magic angle spinning (MAS) NMR spectra can be obtained at a $^{13}$C frequency of 50.3 MHz on e.g., a Varian Unity-200 spectrometer. Samples are packed in a 7 mm diameter cylindrical zirconia rotor with Kel-F end-caps and spun at 5000±100 Hz in a Doty Scientific MAS probe. CP spectra are acquired using a 1-ms contact time and a 0.5-s recycle delay. 10,000-100,000 scans are collected for each spectrum.

DP spectra are acquired using a 6.0-ms (901) $^{13}$C pulse. A recycle delay of 90 seconds is used for all samples and 1000 transients collected for each sample. DP spectra are corrected for background signal. Free induction decays for both CP and DP spectra are acquired with a sweep width of 40 kHz. 1216 data points are collected over an acquisition time of 15 ms. All spectra are zero-filled to 8192 data points and processed with a 50-Hz Lorentzian line broadening and a 0.005-s Gaussian broadening. Chemical shifts are externally referenced to the methyl resonance of hexamethylbenzene at 17.36 ppm.

Spin counting experiments are performed using the method of Smernik and Oades. Glycine can be used as an external intensity standard (i.e. the glycine spectrum was acquired separately to those of the samples). For CP spin counting experiments, differences in spin dynamics between the sample and the glycine standard are accounted for using the method of Smernik and Oades, except that a variable spin lock (VSL) rather than a variable contact time (VCT) experiment is used to determine $T_{1\rho}H$.

VCT and VSL experiments are performed as part of the RESTORE procedure [Smernik and Oades] for determining rates of $T_{1\rho}H$ relaxation and rates of polarization transfer (TCH). VCT experiments can consist of an array of eight contact times (2, 2.5, 3, 4, 5, 6, 8, 10 ms). The experiments are run in an interleaved fashion, with 32 scans acquired for each contact time, in turn. This is repeated until a total of 4000 scans is acquired. A 0.5-s recycle delay can be employed for all samples.

VSL experiments are performed with three different contact times, 200 ms, 1 and 2 ms. For the 200-ms contact time VSL experiments, ten spin lock times are used (0, 0.3, 0.8, 1.3, 1.8, 2.3, 2.8, 3.8, 4.8 and 5.8 ms), for the 1-ms contact time VSL experiments, ten spin lock times are used (0, 0.5, 1, 1.5, 2, 3, 4, 5, 7 and 9 ms) and for the 2-ms contact time VSL experiments, eight spin lock times are used (0, 0.5, 1, 2, 3, 4, 6 and 8 ms). The VSL experiments are run in an interleaved fashion, with blocks of 32 scans acquired in turn, to a total of 4000, with a 0.5-s recycle delay between scans.

Three spectra are acquired as input spectra for generating RESTORE subspectra; a 1-ms contact time—0 spin lock spectrum, a 5- or 6-ms contact time—0 spin lock spectrum, and a 1-ms contact time—1-, 2- or 3-ms spin lock spectrum. These spectra can be acquired in an interleaved fashion, with blocks of 32 scans acquired in turn, to a total of 10,000-25,000, with a 0.5-s recycle delay between scans.

Proof of principle experiments have been attempted and turned out to be successful. However, data points from these early tests were insufficient for rigorous numerical analysis. Nevertheless, the method was a success, and is an improvement over existing methods due to more accurate and complete data.

A set of petroleum source rock samples of different thermal maturities were used. Kerogen isolate was prepared via acid digestion of the source rocks. Bitumen was extracted from source rock and kerogen using dichloromethane as solvent.

Solid-state $^{13}C$ and $^1H$ magic angle spinning (MAS) NMR measurements were performed on a Bruker DSX-300 spectrometer operating at a magnetic field strength of 7.05 T ($^1H$ frequency=300 MHz) using a 4.0 mm Bruker MAS probe. During the measurement, the sample was undergoing magic angle spinning at a rotational speed of 5 kHz. Quantitative $^{13}C$ NMR spectra were obtained using a direct polarization method with high power 1H decoupling at 10 kHz MAS. In order to remove signal background, a double acquisition sequence called Elimination of Artifacts in NMR Spectroscopy (EASY) was utilized.

Figure 4:
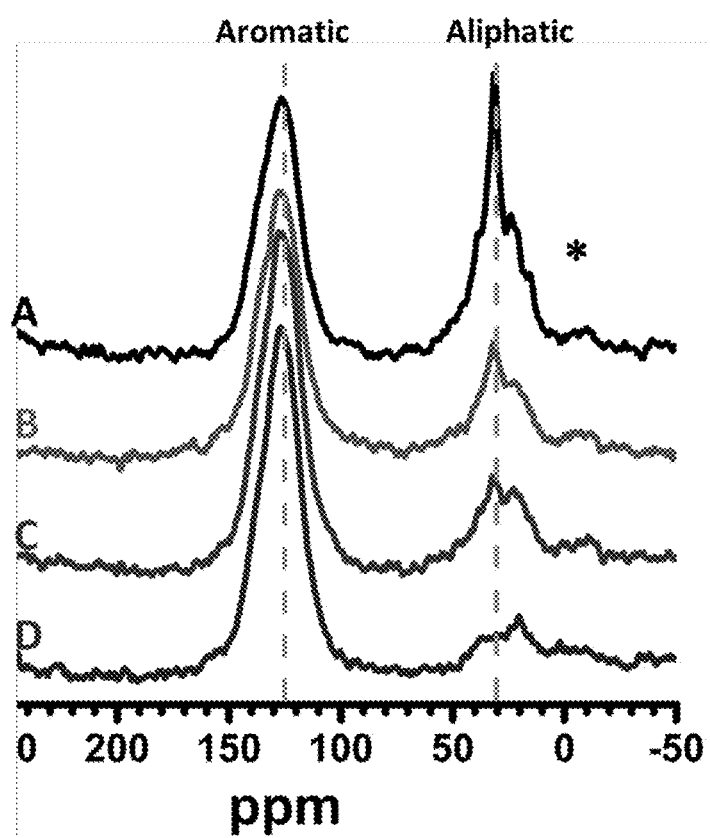
FIG. 4 shows the $^{13}C$ NMR spectra of four isolated kerogen samples of different maturities.

FIG. 4 shows the $^{13}C$ NMR spectra of four isolated kerogen samples of different maturities. As maturity increases from sample A to D, relative intensities of aromatic carbon signal increase while those of aliphatic carbon decrease. The aromatic fraction, $f_{Ar}^{Ker}$, is listed in Table 1. Such quantitative measurements of the changes of aromatic and aliphatic carbon over a given thermal history (temperature and time) allow derivation of the kinetics of the transformation of kerogen to petroleum fluids, and the subsequent alterations of generated petroleum fluids.

$^1H$ NMR analysis can differentiate rigid $^1H$ signal and mobile $^1H$ signal in a given sample. Rigid $^1H$ signal is typically very broad due to dipolar interaction, whereas mobile $^1H$ is much narrower due to averaging out dipolar interactions. Once generated, the majority if not all of the heavier petroleum fluid is absorbed in the kerogen matrix. The true kerogen fabric is rigid and produces rigid $^1H$ signal, while the petroleum fluids absorbed in the kerogen fabric are mobile and produce mobile $^1H$ signal. For these four kerogen samples, the percent of mobile $^1H$ signal is summarized in Table 1. This stands out as a distinctive advantage of NMR based hydrocarbon generation kinetics analysis over conventional kinetics analyses. Conventional compositional kinetics analyses employ tedious and error prone chemical separation procedures, e.g. solvent extraction, filtration, to separate and determine the amount of generated petroleum fluids versa residual kerogen.

Bulk H:C ratio can be readily obtained from NMR analysis. The H:C ratios for these four kerogen samples are summarized in Table 1. Over all, as the kerogen goes through earlier oil window to late gas window, the H:C ratio decreases, fraction of aromatic carbon increases, and the mobile $^1H$ signal decrease, consistent with observations from conventional kinetics analysis experiments.

TABLE 1

Percent of mobile (non-rigid) kerogen measured using 5 kHz $^1H$ MAS NMR, aromatic carbon fraction ($f_{Ar}^{Ker}$) from 10 kHz $^{13}C$ MAS NMR, and the H:C ratio measured with ssNMR

| Sample | $^1H$ Mobile % | $^{13}C f_{Ar}^{Ker}$ | H:C |
|---|---|---|---|
| A | 39.6% | 0.60 | 0.95 |
| B | 20.2% | 0.75 | 0.73 |
| C | 13.4% | 0.80 | 0.65 |
| D | 9.3% | 0.87 | 0.55 |

The following references are incorporated by reference in their entirety for all purposes:

Petsch, et el., A solid state 13C-NMR study of kerogen degradation during black shale weathering, Geochimica et Cosmochimica Acta, Vol. 65, No. 12, pp. 1867-1882 (2001), available online at http://works.bepress.com/cgi/viewcontent.cgi?article=1007&context=steven_petsch Smernik R. J., et al., Assessing the quantitative reliability of solid-state 13C NMR spectra of kerogens across a gradient of thermal maturity, Solid State Nuclear Magnetic Resonance 29 (2006) 312-321, available online at http://www.geo.unizh.ch/~mschmidt/downloads/Smernik2005.pdf.

Smernik, R. J., Oades, J. M., Geoderma 96 (2000) 159.

Smernik, R. J., Oades, J. M., Geoderma 96 (2000) 101.

Smernik, R. J., Oades, J. M., Eur. J. Soil Sci. 54 (2003) 103.

The invention claimed is:

1. A method of determining and using hydrocarbon generation potential from kerogen, said method comprising:
 a) obtaining a sample of kerogen;
 b) performing elemental analysis on a portion of said kerogen to determine its C, H, N, S and O content;
 c) performing nuclear magnetic resonance (NMR) analysis on a portion of said kerogen to determine its initial relative abundances of different H and C species;
 d) pyrolyzing a portion of said kerogen to determine a pyrolysis temperature profile and to produce petroleum fluid and a kerogen residue;
 e) analyzing the composition of said petroleum fluid;
 f) performing NMR analysis on said kerogen residue; and g) predicting hydrocarbon generation from said kerogen using the data obtained in steps b-f to determine the hydrocarbon generating potential of said kerogen; and, h) using said hydrocarbon generating potential in formulating and executing exploration and production plans.

2. The method of claim 1, wherein said NMR analysis is solid state NMR.

3. The method of claim 1, wherein said NMR analysis uses 13C NMR.

4. The method of claim 1, wherein said NMR analysis uses 1H NMR.

5. The method of claim 1, wherein said NMR analysis uses 15N NMR.

6. The method of claim 1, wherein said NMR analysis uses both 13C and 1H NMR.

7. The method of claim 1, wherein said NMR analysis is solid-state magic angle spinning (MAS) NMR.

8. The method of claim 1, wherein said NMR analysis is solid state NMR using cross polarization (CP).

9. The method of claim 1, wherein said NMR analysis is solid state NMR using direct polarization (DP).

10. The method of claim 1, wherein said NMR analysis is solid state NMR using both CP and DP.

11. The method of claim 1, wherein said method uses spin counting to calibrate NMR data.

12. The method of claim 1, wherein predicting step uses a network of first order parallel reactions.

13. The method of claim 1, wherein predicting step uses higher order parallel reactions plus sequential reactions.

14. The method of claim 1, wherein predicting step uses the Arrhenius equation.

15. The method of claim 1, wherein said pyrolyzing step produced a pyrogram that can be read to determine S1, S2, S3, and Tmax.

16. The method of claim 1, wherein said identifying step uses gas chromatography or mass spectrometry or NMR or a combination thereof.

17. The method claim 1, wherein NMR provides relative abundances of rigid H, mobile H and C species.

18. The method of claim 1, wherein gold vessel thermolysis of a portion of said isolated kerogen is performed as a double check of the data.

19. A method of determining and using hydrocarbon generation potential from kerogen, said method comprising:

a) obtaining a sample of source rock containing kerogen;

b) grinding said source rock to produce a powder;

c) extracting said powder to produce isolated kerogen;

d) performing elemental analysis on a portion of said isolated kerogen to determine its C, H, N, S and O content;

e) performing NMR analysis on a portion of said isolated kerogen to determine its initial relative abundances of different H and C species;

f) pyrolyzing a portion of said isolated kerogen to determine a pyrolysis temperature profile and to produce petroleum fluid and a kerogen residue;

g) analyzing the composition of said petroleum fluid;

h) performing NMR analysis on said kerogen residue; and i) predicting hydrocarbon generation potential from said kerogen using the data obtained in steps d-h and using first order parallel reactions or higher order parallel reactions plus sequential reactions; and, j) using said hydrocarbon generating potential in formulating exploration and production plans and using said exploration and production plans in exploring and producing hydrocarbons.

* * * * *